(12) United States Patent
Dasch

(10) Patent No.: US 8,222,896 B2
(45) Date of Patent: Jul. 17, 2012

(54) METHOD AND APPARATUS FOR ANALYZING WELD STRENGTH OF FRICTION STIR SPOT WELDS

(75) Inventor: Cameron John Dasch, Bloomfield Hills, MI (US)

(73) Assignee: GM Global Technology Operations, Detroit, MI (US)

( * ) Notice: Subject to any disclaimer, the term of this patent is extended or adjusted under 35 U.S.C. 154(b) by 460 days.

(21) Appl. No.: 12/577,501

(22) Filed: Oct. 12, 2009
(Under 37 CFR 1.47)

(65) Prior Publication Data
US 2010/0117636 A1    May 13, 2010

Related U.S. Application Data

(60) Provisional application No. 61/113,920, filed on Nov. 12, 2008.

(51) Int. Cl.
*G01R 33/14* (2006.01)
(52) U.S. Cl. ........................... 324/222; 324/238
(58) Field of Classification Search .................... 324/222
See application file for complete search history.

(56) References Cited

U.S. PATENT DOCUMENTS 8,052,029 B1 *  11/2011  Sigler et al. ................. 228/103
2010/0200642 A1 *  8/2010  Burford ..................... 228/112.1

* cited by examiner

*Primary Examiner* — Thomas Valone
(74) *Attorney, Agent, or Firm* — Cantor Colburn LLP

(57) ABSTRACT

On a friction stir spot welded workpiece having a first side including a friction stir spot weld hole and an opposing smooth second side, an eddy current probe is passed over the spot weld hole from the second side, and an eddy current signal representative of a material thickness of the workpiece is produced. The eddy current is analyzed via an eddy current analyzer, and a graphic representation of the analyzed eddy current signal is monitored as the probe passes over the spot weld hole, and a local minima of the graphic representation defined by a displayed characteristic J-shaped curve is identified, the local minima defining a remaining material thickness of the workpiece at the bottom of the spot weld hole. From the graphic representation, a value of the remaining material thickness is determined, and a weld strength of the spot weld as a function of the remaining material thickness is determined.

11 Claims, 12 Drawing Sheets

FSSW Remaining Metal Thickness using Eddy Current

Step 1. Nulling. Hold probe in air. Click here.

Step 2. Calibrate. Place probe on reference sample 1. Click here.

Step 3. Calibrate. Place probe on reference sample 2. Click here.

Step 4. Calibrate. Place probe on reference sample 3. Click here.

Step 5. Measure weld. Place probe on weld. Click here.

Sample #

RESULT

Add comment here after weld measurement. Hit enter.

UNDO LAST WELD    SAVE DATA FILE    QUIT

METHOD AND APPARATUS FOR ANALYZING WELD STRENGTH OF FRICTION STIR SPOT WELDS

CROSS REFERENCE TO RELATED APPLICATIONS

This application claims the benefit of U.S. Provisional Application Ser. No. 61/113,920, filed Nov. 12, 2008, which is incorporated herein by reference in its entirety.

TRADEMARKS

GM® is a registered trademark of General Motors Corporation, Detroit, Mich., U.S.A. Other names used herein may be registered trademarks, trademarks or product names of General Motors Corporation or other companies.

BACKGROUND OF THE INVENTION

The present disclosure relates generally to a method and apparatus for analyzing weld strength of friction stir spot welds, and particularly to using eddy currents for analyzing weld strength of friction stir spot welds in an aluminum workpiece.

Friction stir spot welding (FSSW) uses a rotating tool that is driven through a stack of sheets that are to be welded together. This creates a mechanically mixed region in the sheets that holds the stack together. A hole is left when the tool is extracted. One of the key features of FSSW is the penetration of the tool through the stack into the bottom sheet. The target penetration is roughly half way through the bottom sheet. If the penetration is too shallow, the weld strength is reduced. If the penetration is too deep, the outer surface may be distorted or perforated or the tool and anvil may be damaged. To ensure the quality of welds and to prevent damage to the welder, a nondestructive method for measuring the remaining metal thickness and determining the strength of the weld is needed. Accordingly, the art of friction stir spot welding would be advanced with an improved nondestructive method for measuring the remaining metal thickness and determining the strength of the weld.

BRIEF DESCRIPTION OF THE INVENTION

An embodiment of the invention is a method of analyzing a weld strength of a friction stir spot weld. On a friction stir spot welded workpiece having a first side including a visible friction stir spot weld hole and an opposing second side including a substantially smooth surface in the vicinity of the spot weld hole, an eddy current probe is passed over the spot weld hole from the second side, and an eddy current signal representative of a material thickness of the workpiece is produced therefrom. The eddy current is analyzed via an eddy current analyzer, and a graphic representation of the analyzed eddy current signal is monitored on a display as the probe passes over the spot weld hole, and a local minima of the graphic representation defined by a displayed characteristic J-shaped curve is identified, the local minima defining a remaining material thickness of the workpiece at the bottom of the spot weld hole. From a defined correlation between the graphic representation and the remaining material thickness, a value of the remaining material thickness is determined from the graphic representation. From a defined correlation between weld strength and the remaining material thickness, a weld strength of the spot weld as a function of the remaining material thickness is determined.

An embodiment of the invention is an eddy current analyzer for analyzing a weld strength of a friction stirred spot weld hole on a workpiece. The analyzer includes a housing having a processing circuit, and an eddy current probe in signal communication with the processing circuit. The processing circuit is responsive to computer executable instructions which when executed by the processing circuit facilitates: reading an eddy current signal from the eddy current probe, the signal being representative of a material thickness of the workpiece; and displaying a graphic representation of the signal as the probe passes over the spot weld hole, the graphic representation having a characteristic J-shaped curve including a local minima defining a remaining material thickness of the workpiece at the bottom of the spot weld hole. The value of the remaining material thickness at the bottom of the spot weld hole correlates with a weld strength of the spot weld.

An embodiment of the invention is an apparatus for use with an eddy current analyzer having a processing circuit for analyzing a weld strength of a friction stir spot weld on a workpiece. The apparatus includes an eddy current probe disposed in signal communication with the processing circuit, the probe being configured and adapted to produce an eddy current signal representative of a material thickness of the workpiece, and a spacer disposed at the end of the probe between the probe and the workpiece, the spacer being so configured and dimensioned as to controllably lift off a signal-responsive face of the probe from a surface of the workpiece by a defined amount.

BRIEF DESCRIPTION OF THE APPENDICES

Referring now to the drawings, which are meant to be exemplary and not limiting, and wherein like elements are numbered alike in the accompanying Figures:

FIG. 9 depicts a graphical user interface in accordance with an embodiment of the invention;

DETAILED DESCRIPTION OF THE INVENTION

Figure 1:
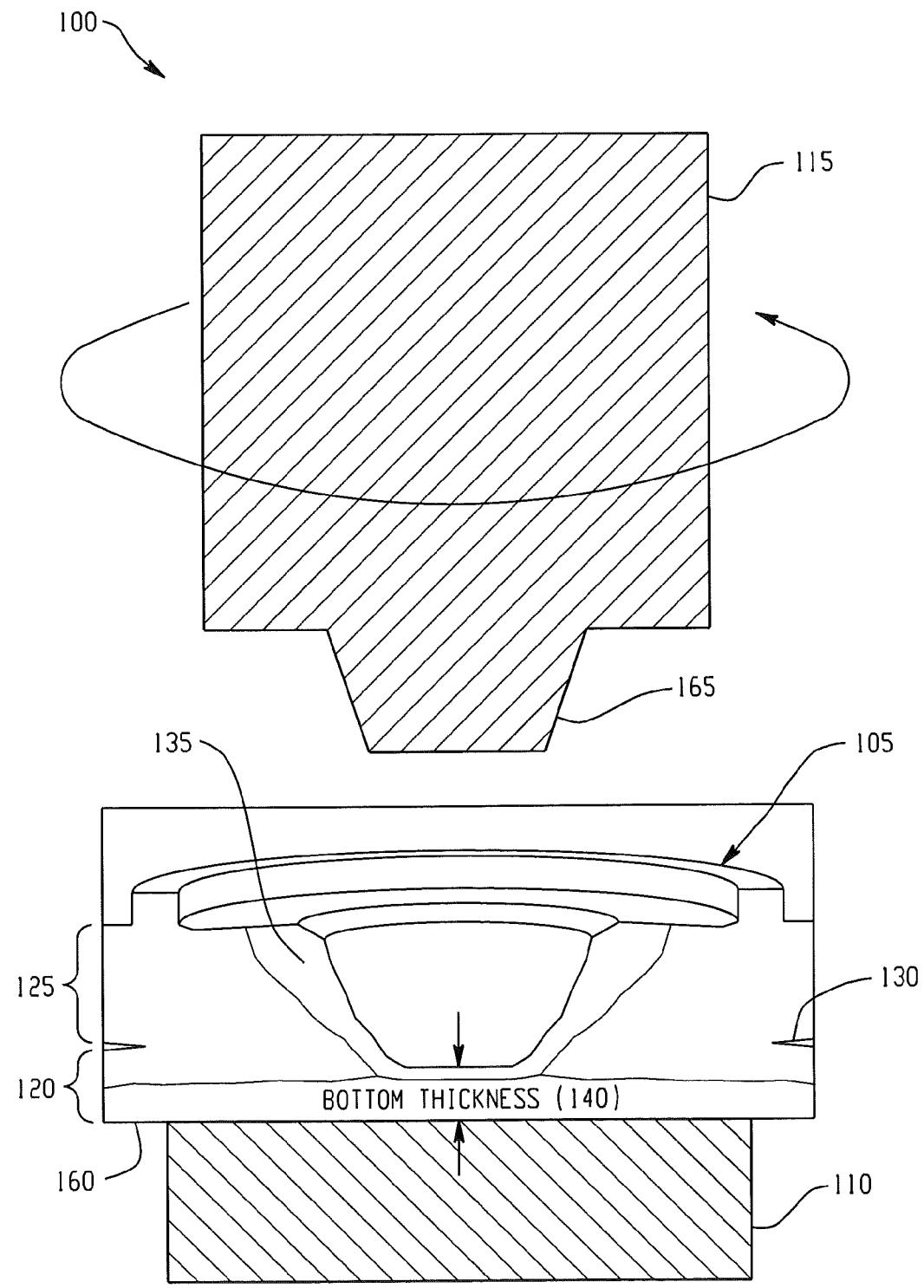
FIG. 1 depicts an example friction stir spot welding apparatus for use in accordance with an embodiment of the invention.

An embodiment of the invention, as shown and described by the various figures and accompanying text, provides a method for inspecting and assessing the quality of friction stir spot welds in a stack of metal sheets that are used in the manufacture of vehicles, especially body structures. These inspections can be used as feedback to the manufacturing process to ensure the quality of the welds, which is largely determined by the depth of penetration of the rotating welding tool through the stack into the lowest sheet. Stated alternatively, the quality of the weld (desired weld strength and surface appearance) can be assessed by determining the remaining metal/material thickness (RMT) at the bottom of the friction stirred spot weld hole. The target penetration of the friction stir spot weld tool is roughly halfway through the lowest sheet.

Embodiments of the invention use an eddy current probe of appropriate size and frequency or frequencies that can accurately measure the remaining metal thickness over a depth that spans the thickness of the lower sheet. Embodiments disclosed herein can measure the remaining metal thickness that may be only 0.1 mm thick. Embodiments of the invention provide a reliable quality control method that can be used either for periodic or 100% inspection of friction stirred spot welds. A simple robust eddy current probe is used that is easy to align with the weld. The probe provides a significant improvement over caliper gauges that require two-sided access, and ultrasonic thickness gauges that typically can not measure less than 0.3 mm thicknesses and have difficulty with the contoured bottom of the hole.

The inspection is performed from the flat bottom surface only ("single-sided"). The measurement method covers a range from 0.1 mm (impending damage to the tool and anvil) to the full thickness of the lower sheet (no weld condition of the bottom sheet). Embodiments employing the measurement method disclosed herein are repeatable and reproducible. For current automotive sheet materials that may be as thin as 0.7 mm, an example acceptance range for the RMT is 0.2 mm to 0.5 mm, with a measurement tolerance of less than 0.05 mm being employed to avoid excessive rejection of good welds.

Embodiments of the invention use a conventional eddy current probe of roughly the same diameter as the FSSW tool pin, which makes the probe relatively insensitive to the location of the weld hole. The frequency of the eddy current is selected to correspond to roughly one skin depth of the lower sheet material. For a lower sheet having thickness L, electrical conductivity s (relative to the Internationally Accepted Copper Standard), and unity relative magnetic permeability as found in nonferric materials, the approximate frequency f needed can be calculated using $f=4370/(L^2 s)$ Hz mm$^2$. This allows remaining metal thicknesses up to the full thickness of the lower sheet to be measured while also giving adequate sensitivity to the thinnest remaining metal thickness. If there is difficulty getting adequate resolution over the entire thickness range, a dual frequency eddy current analyzer may be used, with the high frequency signal being optimized for the thinnest thicknesses and the low frequency signal being optimized for the thicker thicknesses. The dual frequency method is best adapted for nonferric materials. Typically 3-4 calibration samples are employed to calibrate the sensor/analyzer response, which may have a mild temperature sensitivity.

Embodiments of the invention have been implemented for friction stir spot welding of an aluminum hood for a vehicle, where the method covered a thickness range of 0 to 0.8 mm and was subjected to gauge R&R statistical analysis on coupons with resolution of better than 0.05 mm.

In comparison, a variety of ultrasonic thickness gauges and advanced ultrasonic pulse/echo analyzers were tested using a lower thickness range of 0.3 mm, which was determined by the duration of the ultrasonic pulse and the bandwidth of the analyzers. Eddy current arrays were applied to these welds but are 5-6 times more expensive and have unproven depth resolution.

Embodiments of the invention include the use of a conventional dual frequency eddy current analyzer and an appropriate commercial probe. The analyzer was adjusted to give a near-linear response to the remaining metal thickness, and was integrated with a computer that acquired the eddy current signal from the probe, performed a calibration routine, and logged the results.

While embodiments described herein depict aluminum as a workpiece material suitable for friction stir spot welding, upon which the disclosed analysis method and apparatus is applied, it will be appreciated that the disclosed invention is also applicable to other materials suitable for friction stir spot welding, such as magnesium for example.

In view of the invention disclosed herein, it will be appreciated that FSSW weld quality can be determined by measuring the RMT left in the tool pin's hole of a multi-stack spot welded workpiece.

FIG. 1 depicts an apparatus 100 for FSSW having a workpiece 105 disposed between an anvil 110 and a rotary tool 115, with the workpiece 105 having at least two sheets in a stack, illustrated as a lower or bottom sheet 120 and an upper or top sheet 125 with a faying surface 130 therebetween. While FIG. 1 is depicted having only two sheets 120, 125, it will be appreciated from the disclosure herein that this is merely illustrative of an upper and a lower sheet of a stack of sheets that may include a plurality of sheets with the other sheets being disposed between the upper and lower sheets. In practice, for FSSW, once the materials, tool geometry, rotation speed, plunge force and plunge speed are specified, the weld quality is primarily determined by how far the rotary tool 115 penetrates into the lowest sheet 120 of the stack. In FIG. 1, a friction stir spot weld 135 is illustrated having a mechanically mixed region of material centrally arranged with the rotary tool 115, which produces a weld region with a defined bottom remaining material thickness (RMT) 140.

Figure 2:
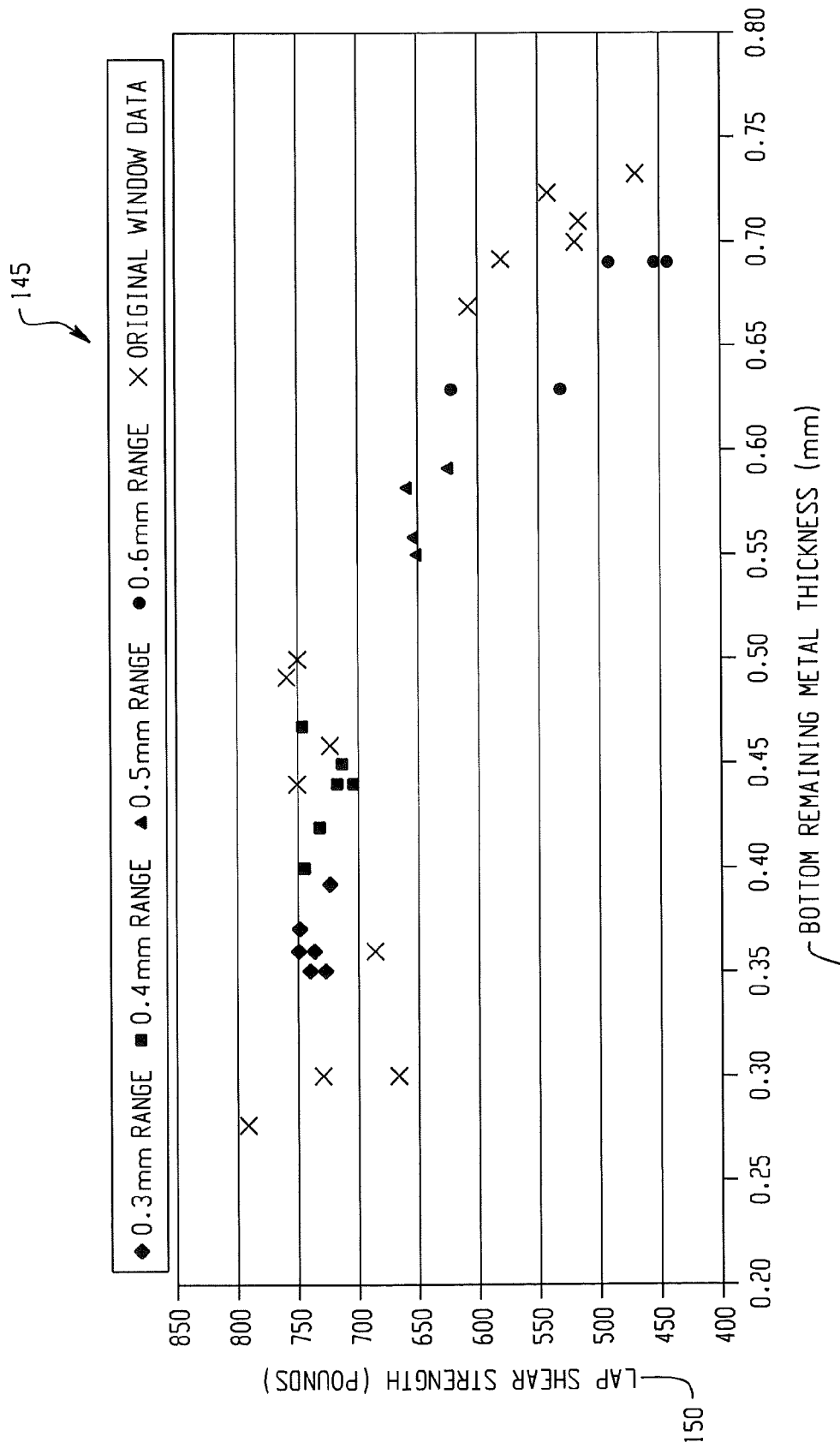
FIG. 2 depicts a chart of data relating lap shear strength of a friction stirred spot weld as a function of remaining material thickness at the bottom of a spot weld for use in accordance with an embodiment of the invention.

As shown in FIG. 2, which illustrates a chart 145 of empirical data of lap shear strength (y-axis) 150 versus bottom RMT (x-axis) 155 for a bottom sheet 120 thickness of 0.8 millimeters (mm), the weld strength typically rises (from right to left on the chart 145) to a peak (at 0.45-0.040 mm for example) as the tool reaches roughly 50% of the lower sheet thickness. The different chart series correspond to different servo settings. In addition to obtaining a peak weld strength condition, it is also important to detect when the FSSW tool 115 penetrates too far into the lower sheet 120. This deep-plunge condition at best leaves a more distorted surface at the bottom surface 160 of the bottom sheet 120 that may be easy to perforate leaving a hole through both sheets 120, 125 (or a plurality of sheets as the case may be). At worse, the rotating tool may catastrophically plunge into the backing anvil 110. Embodiments of the invention are directed to measuring the bottom thickness 140 of the friction stirred spot weld hole 135, alternatively referred to as the remaining metal thickness (RMT).

As mentioned above, an example application includes a lower sheet 120 that is only 0.8 mm thick. In practice, it is fairly difficult to control the tool plunge to a fraction of this thickness, as tool plunge is a difficult parameter to keep in control as heating of the tool during welding may increase the tool length. As a result, a simple inspection approach for FSSW quality in accordance with an embodiment of the invention is to measure the remaining metal thickness 140 of the lower sheet 120. The RMT must be small enough so that a sufficient percentage of the full strength of the weld can be reached, where the RMT is an indirect indicator of that strength. Also, the RMT must be large enough so that the outer skin of the weld site is not prone to perforation. In an example embodiment an acceptable RMT range is 0.20 to 0.65 mm. In order to have as broad an acceptance window as possible, a method with better than 0.05 mm accuracy is desirable.

In connection with embodiments of the invention disclosed herein, empirical data has been generated for five sets of FSSW welds that were prepared with varying bottom thicknesses and with slightly different gauges, alloys, and tool shapes. These welds had a top sheet of aluminum (2.5 mm thickness) and a bottom sheet of aluminum (0.8 mm thickness). All sets used a fixed pin tool, spindle speed, plunge speed, and maximum force. The same basic tool was used for all the welds. The bottom thickness setting was varied to create a full range of welds with bottom thicknesses varying from 0.1 mm to 0.75 mm. Each set included roughly 25 welds. These sets were used for the gauge precision, repeatability, and reproducibility measurements. The bottom thickness of each weld was measured with a fine-tipped external-thickness caliper to 0.01 mm precision.

In an embodiment, the acceptance standard for the friction spot stir welds is based on the variation of lap-shear strength with remaining metal thickness (see FIG. 2). In an embodiment for a lower sheet thickness of 0.8 mm, the weld does not reach maximum strength until the tool plunges to near the middle of the lower sheet. In an embodiment, the maximum allowed RMT is 0.65 mm at which the weld has 80% of maximum strength. In an embodiment, the minimum RMT is not determined by lap-shear strength, but by requiring sufficient metal that a perforation is unlikely. In an embodiment, this lower RMT is 0.2 mm. In an embodiment, the target thickness is 0.45 mm. To provide a flexible acceptance range, welds in the 0.2 to 0.3 mm range and the 0.6 to 0.65 mm range may also be flagged as marginally acceptable.

Figure 3:
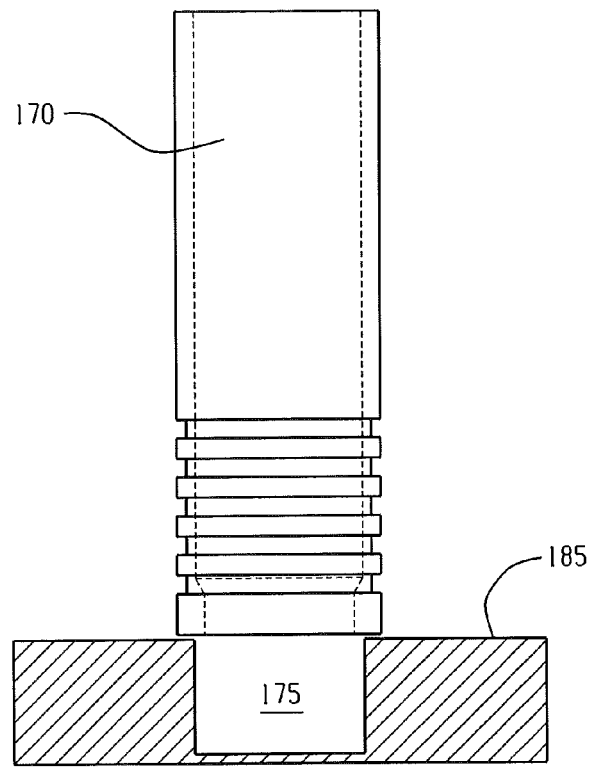
FIG. 3 depicts an eddy current probe in accordance with an embodiment of the invention.

Conventional eddy current inspections use a current loop probe 170, best seen by referring to FIG. 3, to generate an electromagnetic field that partially penetrates into a conducting material. An induced image current (an eddy current) is generated that produces an additional electromagnetic field that is sensed with a pickup coil 175. The coil size and analysis frequency are selected to match the thickness and size of the area to be detected.

For an eddy current field, the amount of penetration, or skin depth, $\delta$ depends on the frequency $\nu$ of the electromagnetic wave, the electrical conductivity $\sigma$ of the sheet, and the magnetic permeability $\mu$ of the sheet:

$$\delta = (\pi \nu \sigma \mu)^{-1/2}$$

For aluminum with relative permeability of 1 and conductivity $\sigma_{IACS}$ expressed as a percent of the International Annealed Copper Standard (IACS), the skin depth is $$\delta 661 \cdot (\nu \sigma_{IACS})^{-1/2} \, mm \cdot (Hz)^{1/2}$$

The analysis frequency must be low enough to give penetration all the way through the lower sheet. In an embodiment, the lower aluminum sheet has a conductivity of 47% IACS and a thickness of 0.80 mm, so that an analysis frequency of approximately 15 kHz is needed to have a skin depth equal to the thickness. In an embodiment the upper aluminum sheet has a conductivity of 34% IACS and does contribute to the eddy current response, though much less than the lower sheet. The measurements are more sensitive for thinner remaining metal thicknesses.

In an embodiment, the hole made by the pin 165 of the weld-tool 115 is 4-6 mm in diameter, which would suggest that a probe with smaller diameter be used. However, there is a physical limitation to making eddy current coil probes with both low frequencies and small diameters and having an overall impedance that matches the input impedance of the eddy current analyzer 180, best seen by referring to FIG. 4. Typical 15 kHz probes have a diameter of 6 mm or larger. Pencil probes with 3 mm coils typically have a lower frequency cutoff of 40 kHz. A range of probes with different diameters and frequency ranges have been tried and from these probes a shielded 8-mm dia. surface probe was selected that provided good thickness resolution, excellent stability, and repeatable positioning. Extensive measurements at 15 kHz with a 3-mm dia. pencil probe working outside its normal range have been made, but it was necessary to re-null the probe on every measurement and the system was too unstable.

Figure 4:
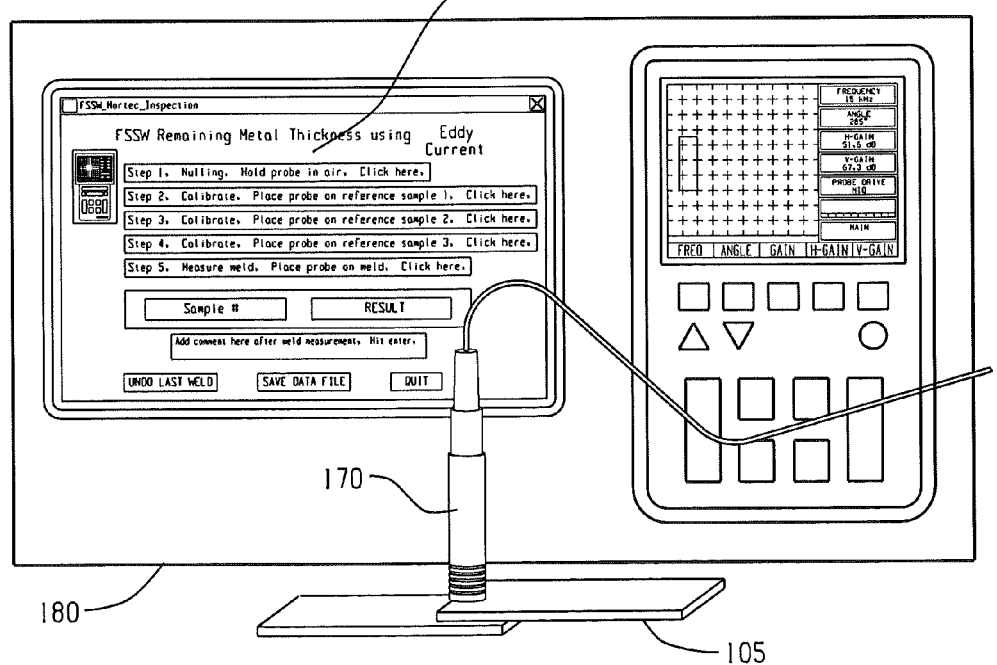
FIG. 4 depicts an eddy current analyzer in accordance with an embodiment of the invention.
Figure 5A:
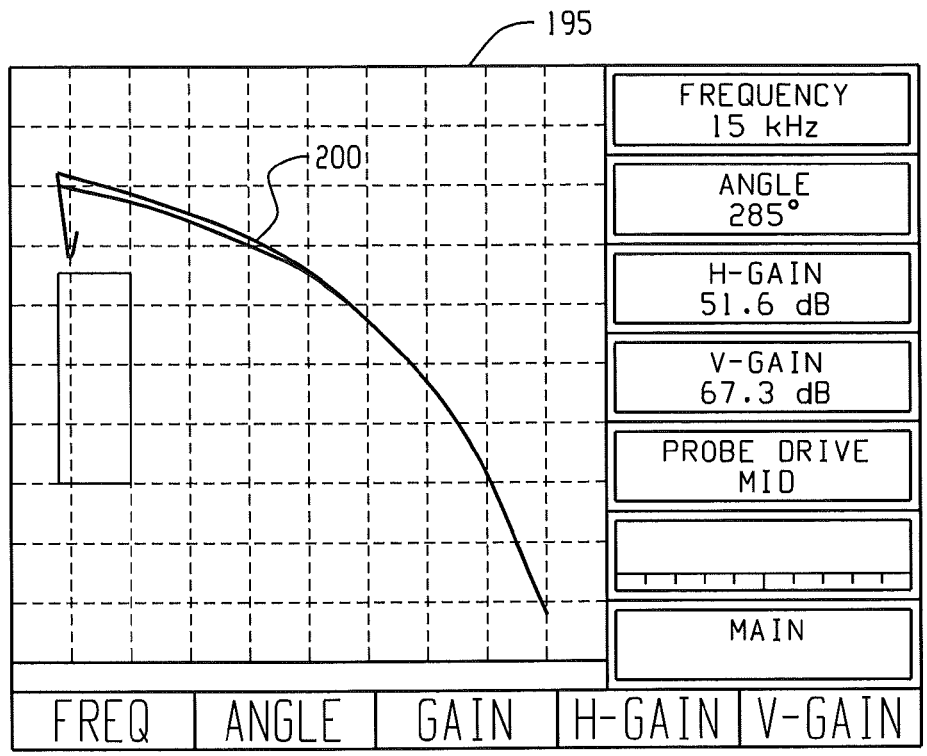
FIGS. 5A, 5B, 5C and 5D depict alternate display windows illustrating a characteristic response signal in accordance with an embodiment of the invention.
Figure 5B:
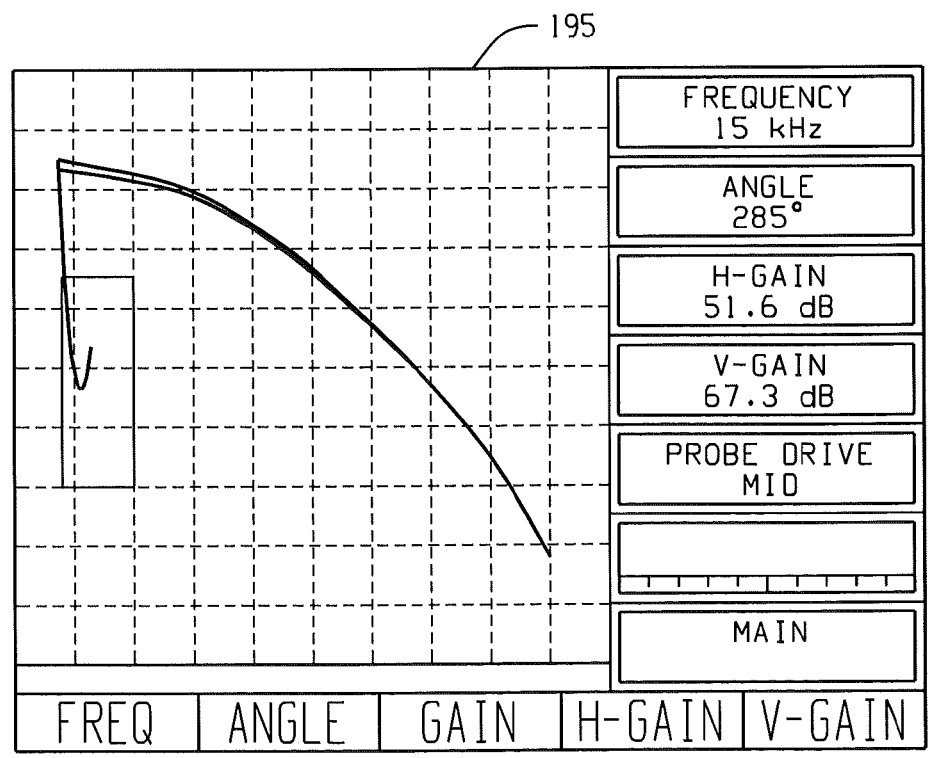
Figure 5C:
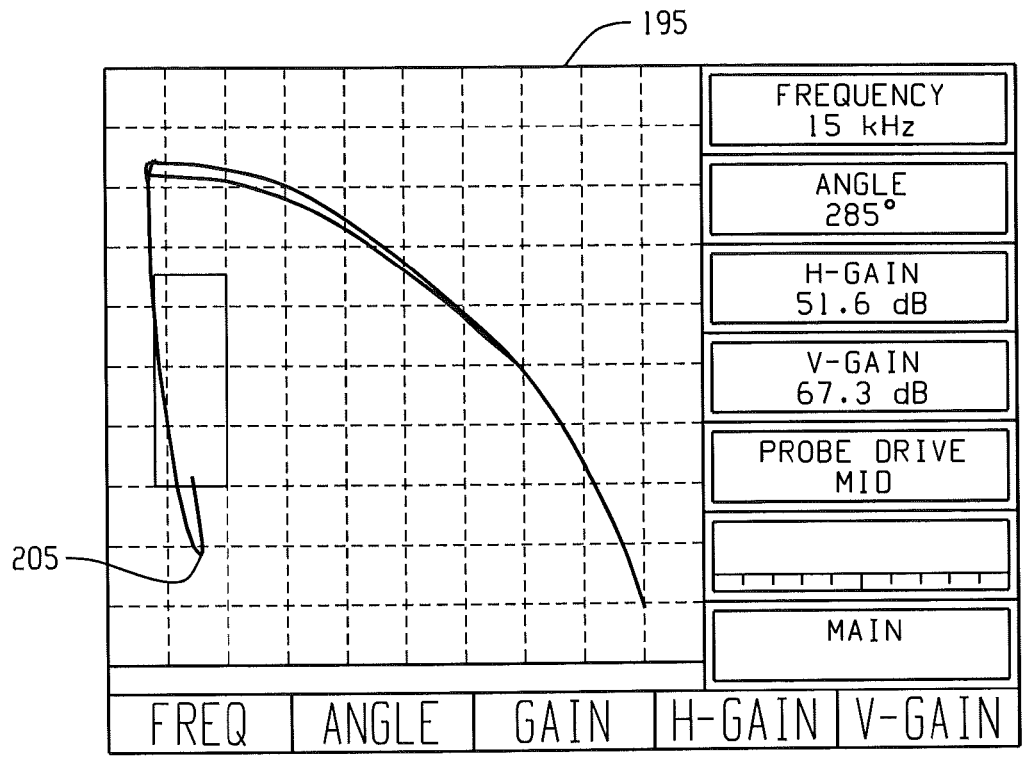
Figure 5D:
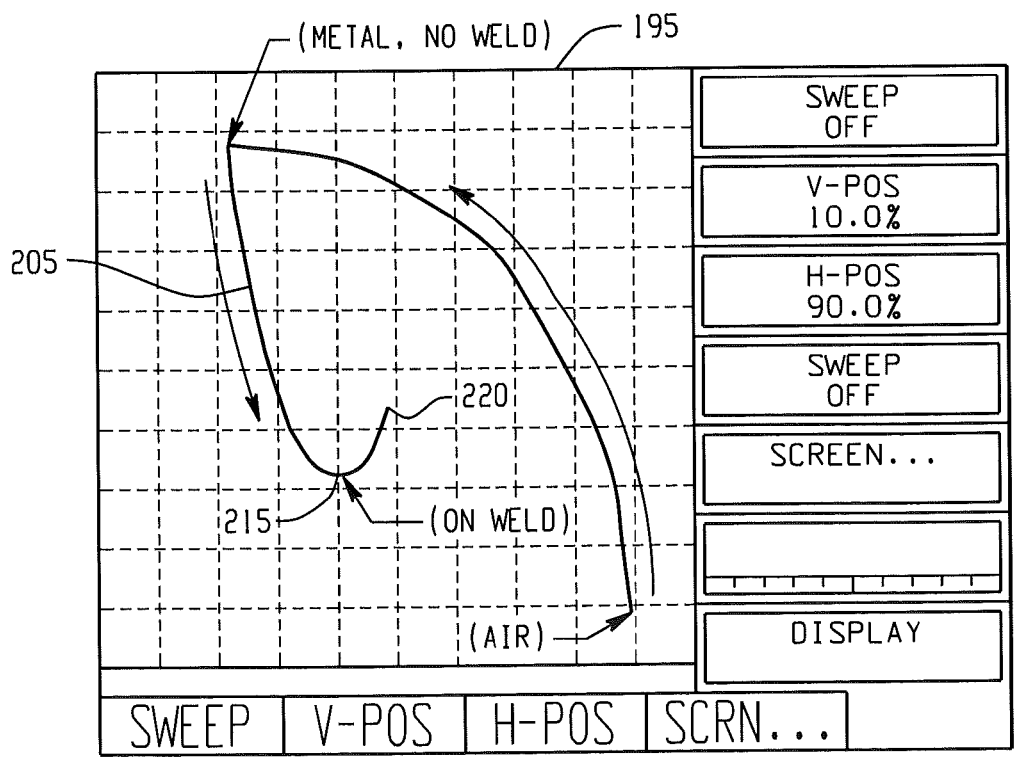

Because the measurement side (anvil-side, or bottom surface 160) of the weld may be slightly roughened, the eddy current probe 170 is mounted in a spacer 185 (see FIG. 3) that lifts the probe slightly off the bottom surface 160. As depicted in FIG. 4, measurement of the bottom surface 160 can be accomplished in a top-down manner by turning the workpiece 105 bottom-up.

For all the test measurements, a commercial eddy current analyzer 180 was used, that is rugged and has a very bright display 190. This analyzer 180 (see FIG. 4) was used in a simple single frequency mode, but also has a conductivity meter and dual-frequency modes. The conductivity feature can be used to quickly test if the correct sheet alloys are being used. The dual-frequency mode can be used in order to increase the precision for the thicker remaining metal thicknesses by using a second lower frequency, which is discussed further below.

The eddy current analyzer 180 is used in, what is known in the art as, a conventional impedance plane display mode. With reference to FIGS. 5A, 5B, 5C and 5D, the null position in air is set to the lower right position (90% right, 10% up) of the display window 195. The phase angle is first coarsely adjusted so that the lift-off curve 200 is horizontally flat when no weld is present. The horizontal and vertical gains are then coarsely adjusted so that the response with no weld is at the upper left position (10% right, 90% up) of the display window 195. The vertical gain and phase rotation are then finely adjusted so that the vertical response to the bottom thickness is approximately linear for three samples that span the acceptance range (0.3 mm, 0.5 mm, and 0.7 mm RMT's).

In an embodiment, only the vertical signal is used to characterize the weld. For the RMT range of 0.3 to 0.6 mm, the response is linear and the analyzer display can be used directly for rough uncalibrated measurements. In this range of 30%-60% of screen height, the RMT corresponds to 0.3 to 0.6 mm. The response becomes fairly nonlinear for RMT's thinner than 0.2 mm. It is contemplated that better precision, especially for thin RMT's, could be obtained if the horizontal signal were also used.

Figure 6:
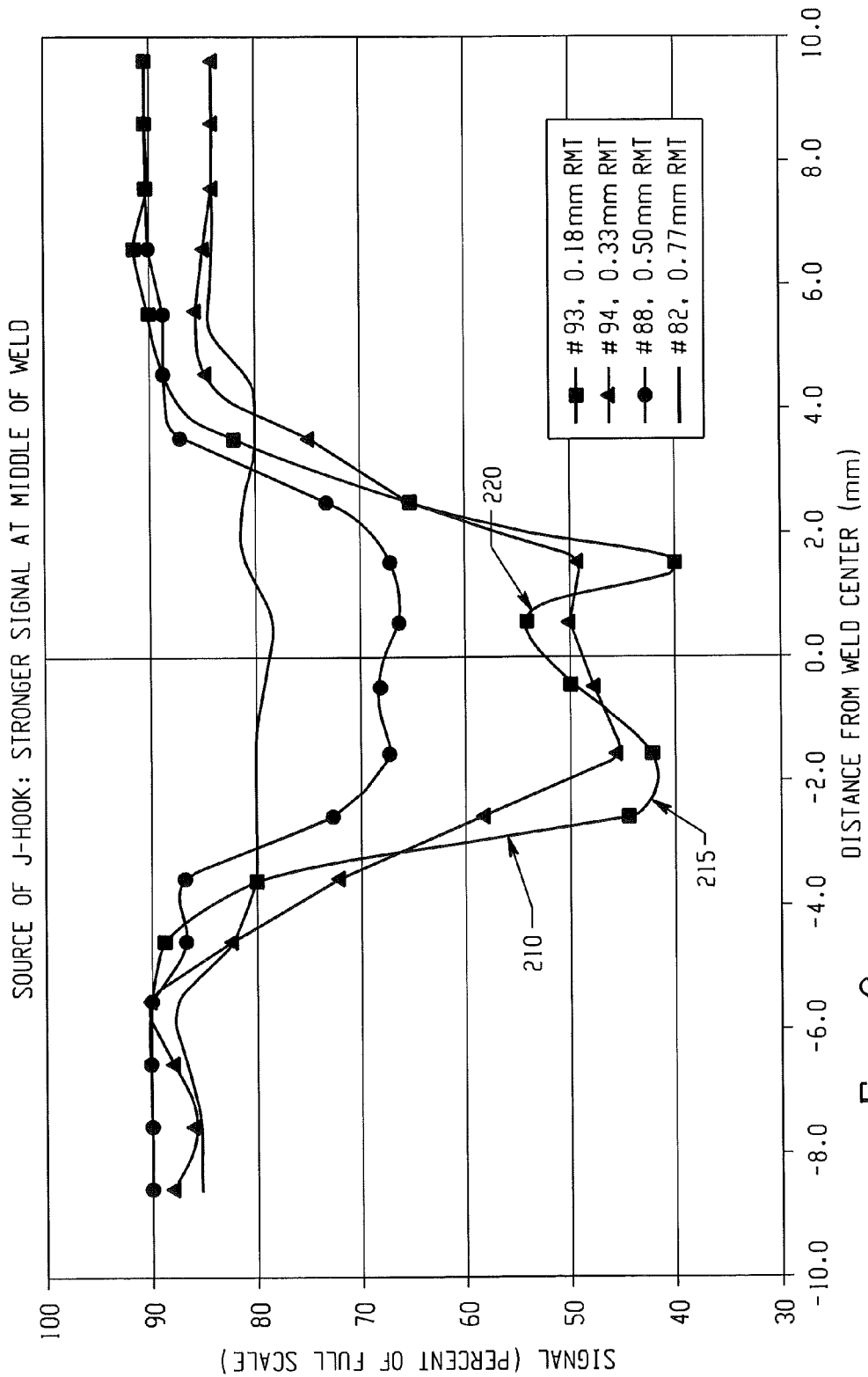
FIG. 6 depicts a graph of data for a several characteristic response signals for different spot welds having different remaining material thicknesses in accordance with an embodiment of the invention.

The eddy current response changes as the probe is moved across the weld. For most of the probes evaluated, and contrary to what may be expected, the maximum response of the probe 170 does not occur at the center of the weld 135. Instead, there is a dip in the response as illustrated in the traces of FIGS. 5A, 5B, 5C, 5D for the selected 8-mm probe. These traces show the response (the liftoff curve 200) as the probe is placed on the weld stack and then slid across the weld 135. The resulting trace from the outer perimeter to the center of weld has a J-shaped hook 205 (best seen with reference to FIGS. 5C, 5D), which has a W-shaped characteristic 210 when passing the probe from one side of the weld to the other side across the weld center (best seen with reference to FIG. 6). The bottom 215 (local minima) of the J-hook (left half of W-characteristic for example) is the most accurately measured response and varies directly with the RMT. The tip 220 (local maxima) of the J-hook actually corresponds to the center of the weld as seen in FIG. 6 where the response as a function of position is plotted. The response at the bottom 215 of the J-hook is used for the measurements, as this reading is less sensitive to probe positioning and occurs over a larger area of the weld.

To compensate for the nonlinear probe response, the response on three samples of known thickness is used to determine a calibration curve. In an embodiment, only the vertical response of the probe is used. The vertical response falls off approximately exponentially in remaining metal thickness t (also herein referred to as RMT) according to the following equation:

$$V = A_{pre} \exp(-t/t_{falloff}) + A_{offset}$$

Using three example calibration coupons of thickness 0.26, 0.51, and 0.74 mm RMT, the three fitting parameters $A_{pre}$, $t_{liftoff}$, and $A_{offset}$ can be determined. These are determined by a least square fit of the three measurements during each calibration.

An example non-limiting set of FSSW inspection requirements includes: measurement of RMT from the bottom of the workpiece in a single-sided measurement manner to ensure weld strength and prevent tool damage; measurement of a typical RMT in the range of 0.1-1.0 mm; measurement of a typical RMT acceptance range of 0.3-0.7 mm; measurement resolution equal to or less than 0.05 mm; measurement repeatability with single inspector; and, measurement reproducibility across multiple inspectors.

Figure 7:
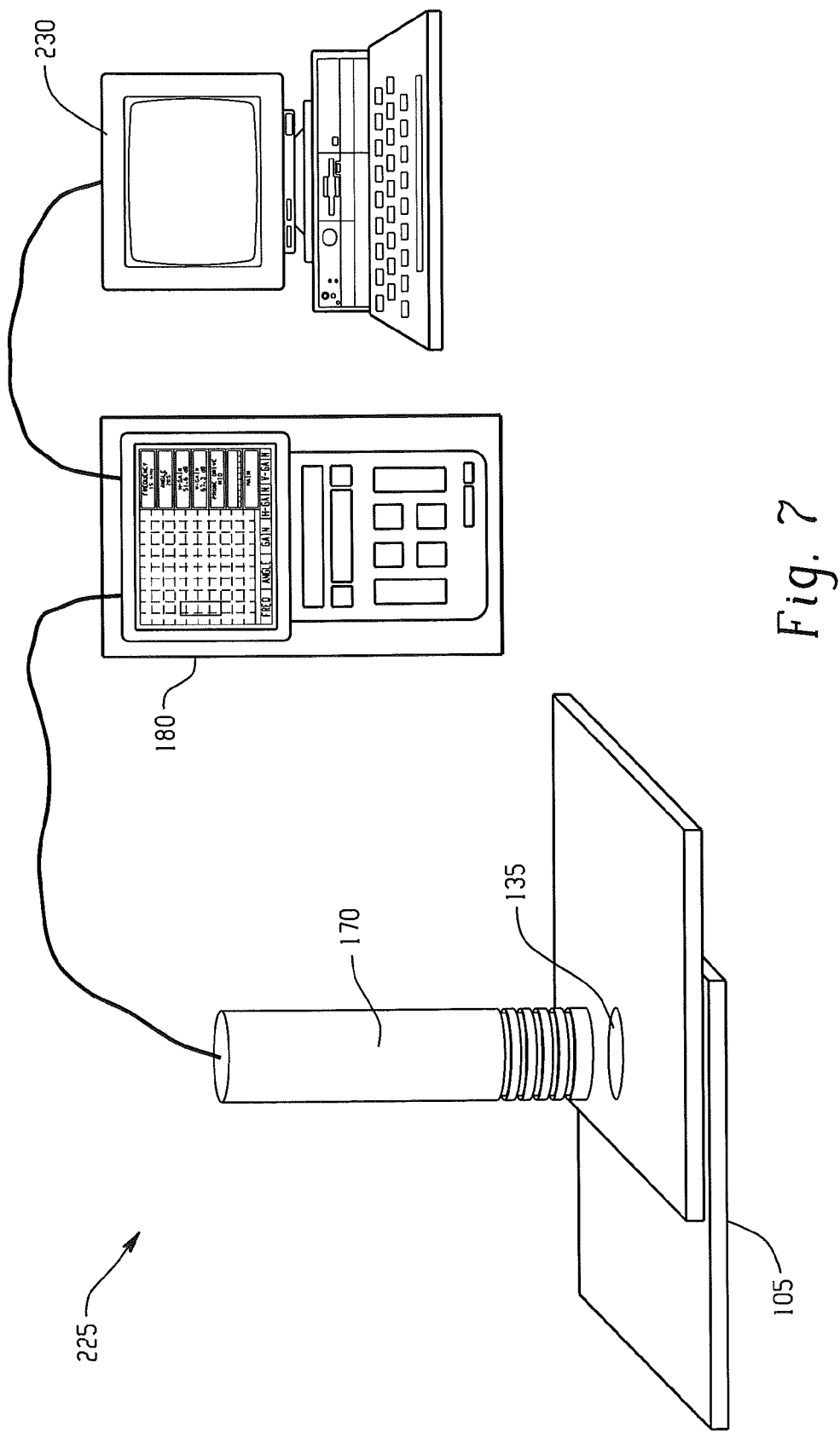
FIG. 7 depicts an example system for practicing embodiments of the invention.

An example system 225 for practicing embodiments of the invention is disclosed in FIG. 7, which includes the above mentioned probe 170 and analyzer 180, and also includes a computer 230, or other suitable processing circuitry, for performing calibration correction and data logging, or any other computing processes as may be disclosed herein.

Figure 8:
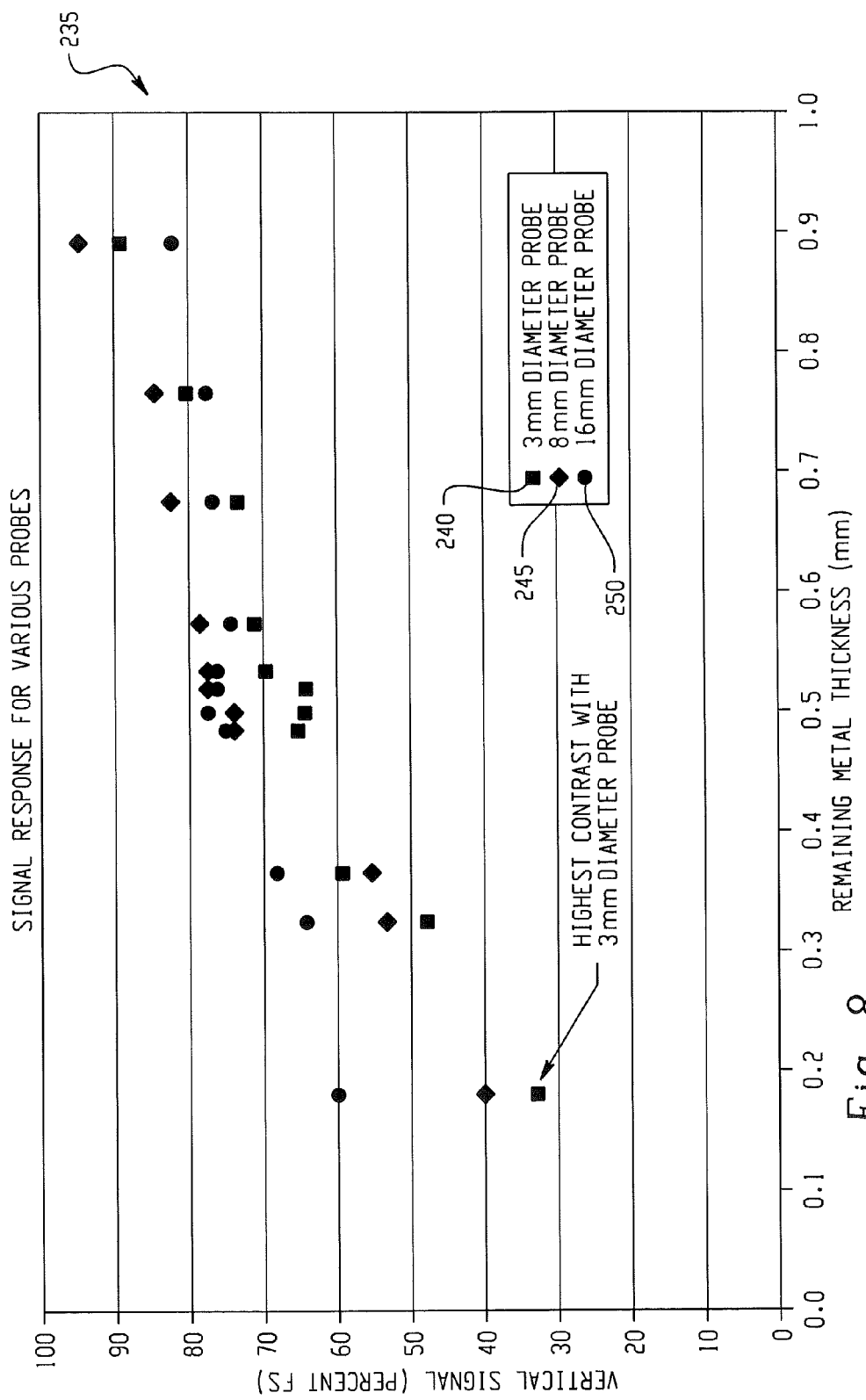
FIG. 8 depicts a chart of data for several characteristic response signals using different eddy current probe diameters in accordance with embodiments of the invention.

FIG. 8 illustrates a chart 235 depicting example signal responses 240, 245 and 250 (vertical signal response as percentage of Full Scale (FS) on the y-axis, versus RMT 140 on the x-axis) for various probes having probe diameters of 3 mm, 8 mm and 16 mm, respectively, in accordance with embodiments of the invention. As discussed above, a shielded 8 mm diameter surface probe was selected that provided good thickness resolution, excellent stability, and repeatable positioning.

FIG. 9 depicts an example graphical user interface (GUI) 255 for use with computer 230 in accordance with an embodiment of the invention. Here, five process steps are depicted via graphical control features (boxes for example): step-1, nulling, where the probe 170 is held in the air, and a reading taken; step-2, calibration-1, where the probe 170 is placed on a reference sample-1 of known thickness-1 and a reading taken; step-3, calibration-2, where the probe 170 is placed on a reference sample-2 of known thickness-2, and a reading taken; step-4, calibration-3, where the probe 170 is placed on a reference sample-3 of known thickness-3, and a reading taken; and, step-5, measurement, where the probe is placed on a weld, and a reading taken. In an embodiment, activation of one of the process steps is accomplished by way of manually touching the GUI (display screen upon which the GUI is displayed) at the associated graphical control feature. However, another embodiment may accomplish activation by using a computer mouse (known in the art) and mouse click operation after placing a mouse cursor over the associated graphical control feature. During step-5, the probe 170 is moved across the bottom surface 120 proximate the weld 135 to display the J-hook 205, as discussed above, and a reading taken when displayed signal indicates the bottom (local minima) 215 of the weld 135. While steps 2-4 indicate a three-point calibration process, other calibrations may be done using a four-point process, or a process using more than four points.

Figure 10:
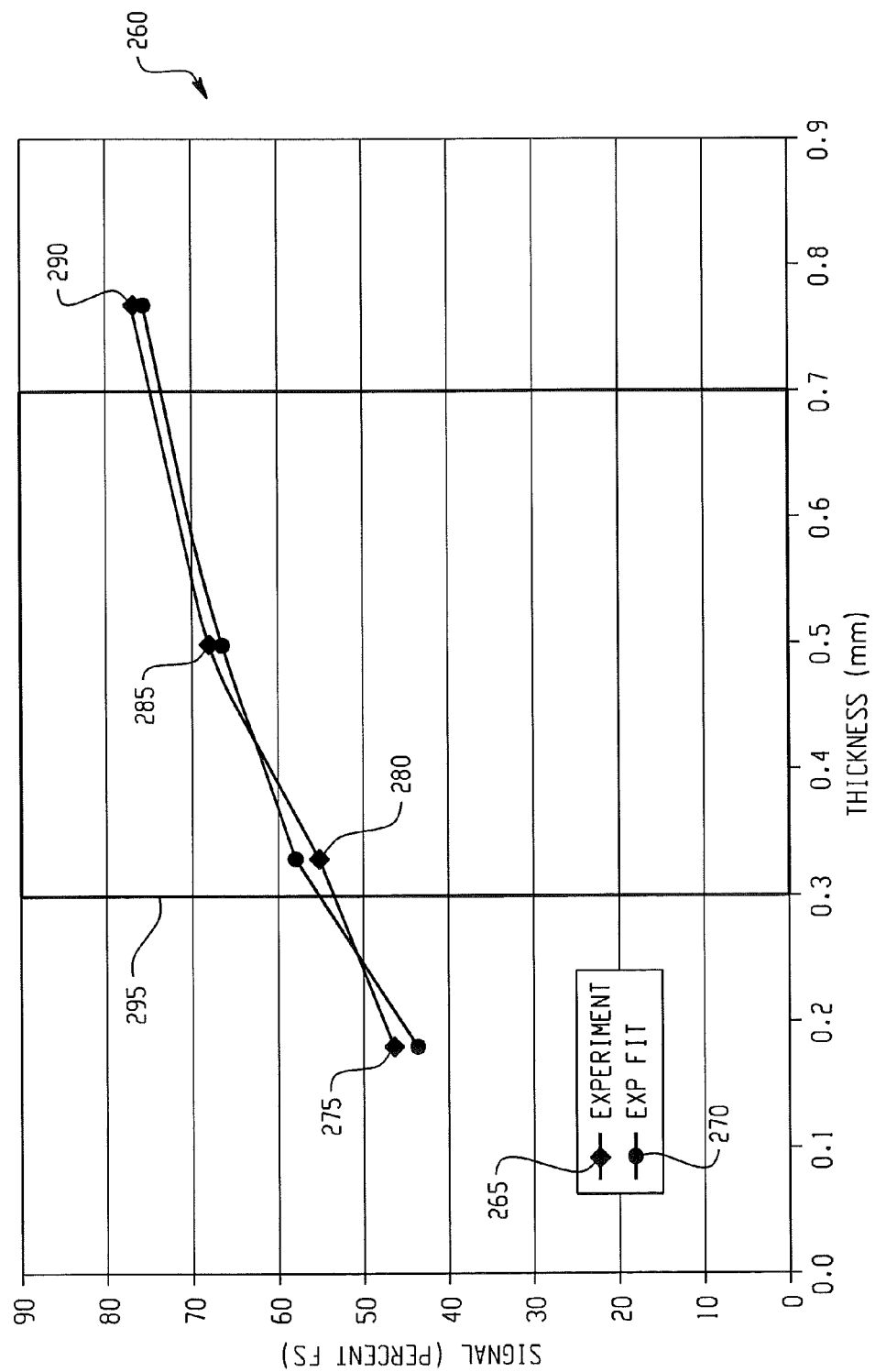
FIG. 10 depicts an example four-point calibration curve in accordance with an embodiment of the invention.
Figure 11:
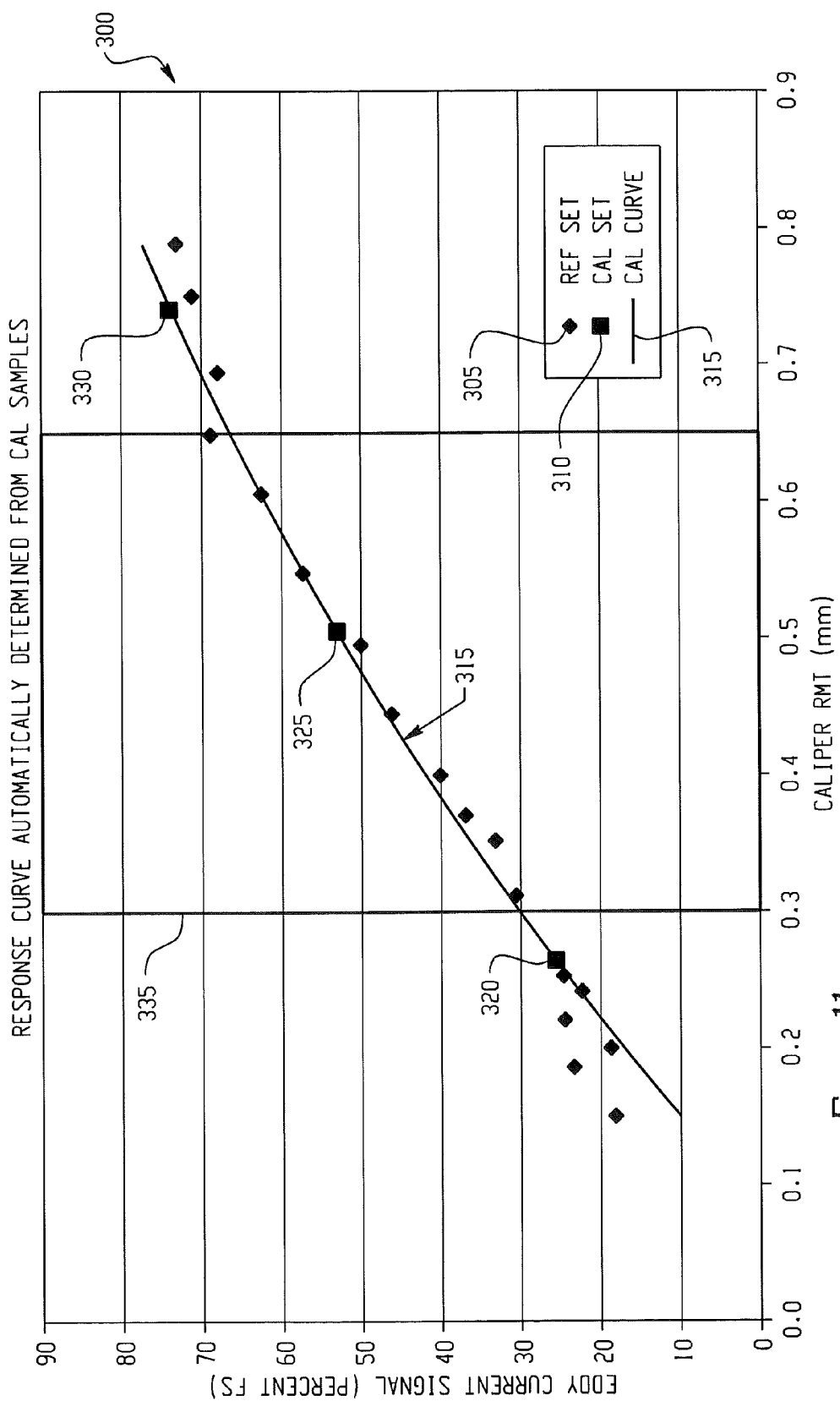
FIG. 11 depicts an example three-point calibration curve in accordance with an embodiment of the invention.
Figure 12:
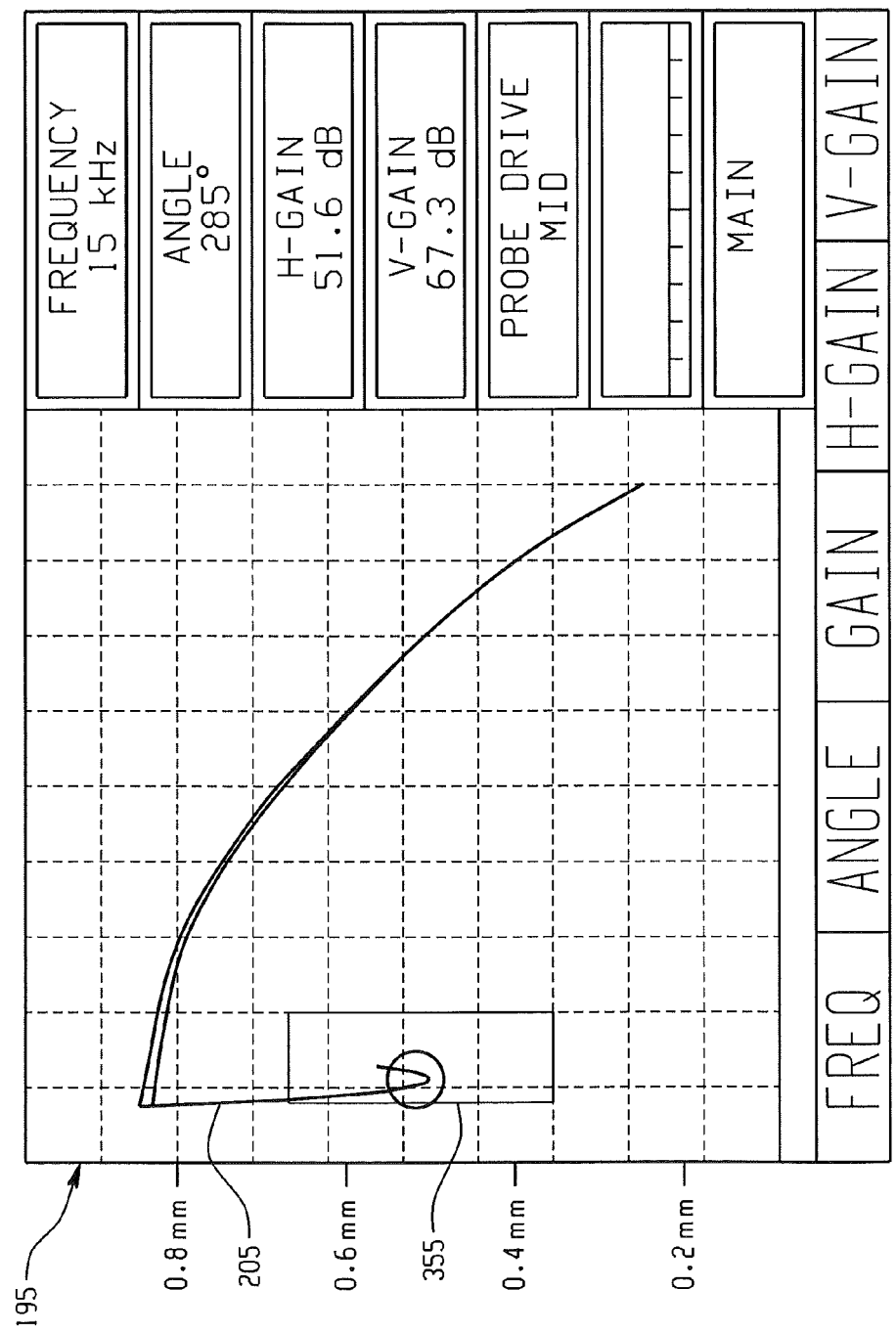
FIG. 12 depicts a similar display window as that of FIGS. 5A, 5B, 5C and 5D for use in accordance with an embodiment of the invention.

FIG. 10 illustrates a typical four-point calibration curve 260 in accordance with an embodiment of the invention, where both calibration data 265 and a curve fit 270 is illustrated. Here, the left-most calibration data point 275 and the right-most calibration data point 290 are outside a target calibration window 295, while the two central calibration data points 280, 285 are within the target calibration window 295. In a similar manner to that of FIG. 10, FIG. 11 depicts a chart 300 illustrating a three-point curve 315 in accordance with an embodiment of the invention, where both experimental data 305 and three-point calibration data 310 are illustrated. In FIG. 11, the x-axis is caliper reading of RMT in millimeters (mm), and the y-axis is eddy current signal (percentage of Full Scale, FS). Here, the left-most calibration data point 320 and the right-most calibration data point 330 are outside a target calibration window 335, while the central calibration data point 325 is within the target calibration window 335. In view of the foregoing four-point and three-point calibration curves, an embodiment of the invention includes a calibration process that includes three or more calibration data points with at least one data point being outside a target calibration window on the low side of the RMT, at least one data point being outside the target calibration window on the high side of the RMT, and at least one data point being inside the target calibration window. As illustrated in FIG. 11, the signal drops from right-to-left as the bottom thickness (RMT) thins. Applying this reduction-in-signal characteristic to a measurement process, and with reference now to FIGS. 7 and 5D in combination with FIG. 12, the probe 170 is slid across the bottom surface 160 across the weld 135 of workpiece 105, and the analyzer 180 watched for the characteristic J-shaped hook 205 (see FIGS. 5D and 12). In an embodiment, an acceptance box 355 that signifies the presence of a weld 135 may be used that spans a vertical signal equivalent to a material thickness reading that ranges from 0.3 mm to 0.65 mm. In an embodiment, and as depicted in FIG. 12, the vertical scale of the display window 195 is set up to approximate the material thickness, in this case the RMT, in 0.1 mm increments.

While certain combinations of structural features or method steps have been described herein, it will be appreciated that these certain combinations are for illustration purposes only and that any combination of any of the structural features or method steps disclosed herein may be employed in accordance with an embodiment of the invention. Any and all such combinations are contemplated herein and are considered within the scope of the invention disclosed.

An embodiment of the invention may be embodied in the form of computer-implemented processes and apparatuses for practicing those processes. The present invention may also be embodied in the form of a computer program product having computer program code containing instructions embodied in tangible media, such as floppy diskettes, CD-ROMs, hard drives, USB (universal serial bus) drives, or any other computer readable storage medium, such as random access memory (RAM), read only memory (ROM), erasable programmable read only memory (EPROM), or electrically erasable programmable read only memory (EEPROM), for example, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to analyze a weld strength of a friction stir spot weld using an eddy current probe and analyzer, the weld strength correlating with a remaining metal thickness at the bottom of the friction stir spot weld hole.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of analyzing a weld strength of a friction stir spot weld, the method comprising:
   on a friction stir spot welded workpiece having a first side comprising a visible friction stir spot weld hole and an opposing second side comprising a substantially smooth surface in the vicinity of the spot weld hole, passing an eddy current probe over the spot weld hole from the second side, and producing therefrom an eddy current signal representative of a material thickness of the workpiece;
   analyzing the eddy current via an eddy current analyzer and monitoring on a display a graphic representation of the analyzed eddy current signal as the probe passes over the spot weld hole, and identifying a local minima of the graphic representation defined by a displayed characteristic J-shaped curve, the local minima defining a remaining material thickness of the workpiece at the bottom of the spot weld hole;
   from a defined correlation between the graphic representation and the remaining material thickness, determining from the graphic representation a value of the remaining material thickness; and
   from a defined correlation between weld strength and the remaining material thickness, determining a weld strength of the spot weld as a function of the remaining material thickness.

2. The method of claim 1, wherein the workpiece comprises at least an upper sheet material and a lower sheet material, and further comprising:
   selecting a frequency of the eddy current probe to correspond to one skin depth of the lower sheet material.

3. The method of claim 1, wherein the workpiece comprises at least an upper sheet material and a lower sheet material, the upper sheet material having a thickness greater than a thickness of the lower sheet material, wherein the eddy current analyzer is a dual frequency eddy current analyzer, and further comprising:
   selecting a first frequency of the eddy current probe to correspond to one skin depth of the lower sheet material;
   selecting a second frequency of the eddy current probe to correspond to one skin depth of the upper sheet material;
   selecting a first frequency of the eddy current analyzer optimized for the lower sheet material thickness, and selecting a second lower frequency of the eddy current analyzer optimized for the upper sheet material thickness.

4. The method of claim 1, further comprising:
   prior to the passing an eddy current probe over the spot weld hole from the second side, performing three calibration tests producing three data points of eddy current signal versus three known and different material thicknesses to calibrate the eddy current probe and the eddy current analyzer;
   wherein a first of the data points is outside of a thickness acceptance window on a low side of an acceptable thickness, a second of the data points is outside of the thickness acceptance window on a high side of an acceptable thickness, and a third of the data points is inside of the thickness acceptance window.

5. The method of claim 1, further comprising:
   prior to the passing an eddy current probe over the spot weld hole from the second side, performing four calibration tests producing four data points of eddy current signal versus four known and different material thicknesses to calibrate the eddy current probe and the eddy current analyzer;
   wherein a first of the data points is outside of a thickness acceptance window on a low side of an acceptable thickness, a second of the data points is outside of the thickness acceptance window on a high side of an acceptable thickness, and a third and a fourth of the data points is inside of the thickness acceptance window.

6. An eddy current analyzer for analyzing a weld strength of a friction stirred spot weld hole on a workpiece, the analyzer comprising:
   a housing comprising a processing circuit;
   an eddy current probe in signal communication with the processing circuit;
   the processing circuit being responsive to computer executable instructions which when executed by the processing circuit facilitates:

reading an eddy current signal from the eddy current probe, the signal being representative of a material thickness of the workpiece; and displaying a graphic representation of the signal as the probe passes over the spot weld hole, the graphic representation comprising a characteristic J-shaped curve comprising a local minima defining a remaining material thickness of the workpiece at the bottom of the spot weld hole;

wherein the value of the remaining material thickness at the bottom of the spot weld hole correlates with a weld strength of the spot weld.

7. The eddy current analyzer of claim 6, wherein the eddy current probe comprises a spacer disposed in a manner that lifts an end of the probe off of a bottom surface of the workpiece being analyzed.

8. The eddy current analyzer of claim 6, further comprising a display screen in signal communication with the processing circuit, the display screen displaying a graphical user interface comprising graphical control features for calibrating the eddy current probe.

9. The eddy current analyzer of claim 8, wherein the graphical control features comprise a first graphical control feature for nulling the eddy current probe, a second, a third and a fourth graphical control feature for calibrating the eddy current probe, and a fifth graphical control feature for measuring the remaining material thickness of the weld.

10. An apparatus for use with an eddy current analyzer comprising a processing circuit for analyzing a weld strength of a friction stir spot weld on a workpiece, the apparatus comprising:

an eddy current probe disposed in signal communication with the processing circuit, the probe being configured and adapted to produce an eddy current signal representative of a material thickness of the workpiece; and a spacer disposed at the end of the probe between the probe and the workpiece, the spacer being so configured and dimensioned as to controllably lift off a signal-responsive face of the probe from a surface of the workpiece by a defined amount.

11. The apparatus of claim 10, wherein the spacer comprises a centrally disposed hole so configured and dimensioned as to reduce signal-error-generating-effects associated with tilt, roughness, or wear of or between the spacer and the surface of the workpiece.

* * * * *